(12) United States Patent
Sandhu

(10) Patent No.: US 6,485,426 B2
(45) Date of Patent: Nov. 26, 2002

(54) NEEDLE GUIDE FOR ULTRASOUND TRANSDUCER

(76) Inventor: NavParkash Sandhu, 67-50A 195th La., Fresh Meadows, NY (US) 11365

( * ) Notice: Subject to any disclaimer, the term of this patent is extended or adjusted under 35 U.S.C. 154(b) by 0 days.

(21) Appl. No.: 09/808,297

(22) Filed: Mar. 14, 2001

(65) Prior Publication Data

US 2002/0133079 A1 Sep. 19, 2002

(51) Int. Cl.[7] .................................................. A61B 8/14
(52) U.S. Cl. ......................................................... 600/461
(58) Field of Search ................................. 600/437, 443, 600/459–461, 564; 606/50, 27, 32, 37, 38–52; 604/900.53; 507/115; 128/638, 639

(56) References Cited

U.S. PATENT DOCUMENTS

| | | | |
|---|---|---|---|
| 4,567,896 A | * | 2/1986 | Barnea et al. .............. 600/443 |
| 4,838,506 A | | 6/1989 | Cooper |
| 4,899,756 A | | 2/1990 | Sonek |
| 5,052,396 A | | 10/1991 | Wedel et al. |
| 5,076,279 A | | 12/1991 | Arenson et al. |
| 5,623,931 A | | 4/1997 | Wung et al. |
| 5,647,373 A | * | 7/1997 | Paltieli ....................... 600/461 |
| 5,758,650 A | | 6/1998 | Miller et al. |
| 5,820,552 A | * | 10/1998 | Crosby et al. .............. 128/915 |
| 5,924,992 A | | 7/1999 | Park et al. |
| 5,928,219 A | | 7/1999 | Friend et al. |
| 5,941,889 A | | 8/1999 | Cermak |
| 6,048,321 A | * | 4/2000 | McPherson et al. ........ 600/564 |
| 6,063,085 A | * | 5/2000 | Tay et al. .................... 606/50 |

* cited by examiner

Primary Examiner—Marvin M. Lateef
Assistant Examiner—Ali M. Imam
(74) Attorney, Agent, or Firm—Bierman, Muserlian and Lucas

(57) ABSTRACT

A needle guidance device for use with an ultrasound transducer is made up of a frame for housing the transducer, a needle guide unit which has a sleeve in line with an ultrasound beam and two arms which affix the frame to the needle guide unit.

13 Claims, 4 Drawing Sheets

NEEDLE GUIDE FOR ULTRASOUND TRANSDUCER

BACKGROUND OF INVENTION

1. Field of Invention

The present invention relates to an apparatus for keeping a needle aligned under an ultrasound beam and, more particularly, for guiding a needle used for administering anesthetic.

2. Prior Art to Invention

Ultrasound systems for real time visual guidance of a needle into a patient's body are known and have been utilized for biopsies, drainage of fluids, amniocentesis, and the like. Generally, the physician uses one hand to hold the transducer against the body of the patient to visualize the target, and the other hand to guide the needle into the patient and hit the target. The ultrasound beam is planar in nature and visualizes the target and the needle as it comes close to the target.

In order to steady the relative position of the transducer, the ultrasound beam, and the needle, various apparatuses have been suggested, see U.S. Pat. Nos. 4,899,756; 5,052,396; 5,076,279; 5,623,931; 5,758,650; 5,924,992; 5,928,219; and 5,941,889. Each of these devices requires that it be affixed to the transducer. Only the device described in the '756 patent allows for independent horizontal movement of the transducer and the needle guidance portion of the apparatus. However, in the '756 patent, the alignment of the needle with the planar ultrasound beam is dependent upon the stability of a single articulating arm. The joint of the articulating arm is connected by a single nut and bolt. Such a joint can come loose and fail to maintain proper alignment of the needle. Naturally, this can lead to problems during a medical procedure.

There is a need for an apparatus which holds and guides the needle while holding the transducer and allows for steady relative horizontal movement of the needle and the transducer.

SUMMARY OF INVENTION

An apparatus for guiding a needle in conjunction with an ultrasound imaging system has now been discovered which securely holds both the needle and the transducer and allows for steady relative horizontal movement between the needle and the transducer. The apparatus of the present invention provides steady movement and securely holds both the transducer and the needle guide during use by employing two parallel arms between which both the transducer and the needle guidance unit are held. These two arms while securely holding both the transducer and the needle guidance unit, allow for relative horizontal movement of the transducer and the needle guidance unit.

Additionally, the present invention employs a box-shaped frame in which the transducer is securely held. By holding rather than affixing the box-shaped frame to the transducer, the speed at which the apparatus is set up for use is greatly accelerated. The transducer is enclosed within a latex bag or other similarly made bag for sterility. Alternatively, a latex sleeve is affixed to the top of the frame such that the latex sleeve, in combination with the frame, encloses the transducer in a sterile manner.

Broadly, the present invention is a needle guidance apparatus for use with an ultrasound imaging device that generates a substantially planar ultrasound beam from one end of a transducer comprising:

(a) a box-shaped frame for securely holding a transducer when the frame with transducer therein is placed against a body of a patient;

(b) a needle guide unit having a sleeve for accommodating and guiding a needle into the body of a patient, said sleeve being coplanar with said ultrasound beam; and (c) two parallel arms, one end of each of said arms attached to opposite sides of said frame and the other end of each of said arms attached to opposite sides of said needle guide unit, said needle guide unit pivoting around a transverse axis, said frame, or said needle guide unit, or both said frame and said needle guide unit being movable with respect to arms such that horizontal distance between said needle guide unit and said frame can be varied.

Preferably, said arms, said frame, and said transverse axis of said needle guide unit are in the same transverse plane.

In order to vary the horizontal distance between the frame and the needle guide unit, each arm has either a slit that runs lengthwise in the arm or a line of holes which also runs lengthwise in the arm. The frame, or the needle guide unit, or both the frame and the needle guide unit have releasable fasteners on their opposite sides which mate with the slot or holes and allow for relative movement.

The arms can be an extension of the frame. In such an embodiment, the needle guide unit is horizontally moveable relative to the frame as well as pivotal between said arms.

In a preferred embodiment, the opposite sides of the frame are parallel sides with outward flat surfaces which are affixed to the respective inside, flat surfaces of the arms. Having the two flat surfaces against each other increases the overall stability and rigidity of the apparatus. Likewise, in the needle guide unit, the two opposite sides are flat parallel sides which are held flat against the inside, flat surfaces of the arms, also increasing the stability and rigidity of the apparatus.

The stability and security of the apparatus of the present invention is provided by the two arms and the orientation of the various components. The arms are oriented to be in two separate parallel vertical planes. The two vertical planes are also parallel to the plane of the ultrasound beam. The ultrasound beam is coplanar with the sleeve and, hence, the needle during insertions. Also, the axis of rotation of the needle guide unit, the two arms and the frame are, preferably, in the same transverse plane. The transverse plane forms a 90° angle with the two vertical planes of the arms and the vertical plane of the ultrasound beam and the sleeve.

These and other aspects of the present invention may be more fully understood by reference to one or more of the following drawings and the detailed description which follows therefrom.

DETAILED DESCRIPTION OF INVENTION

Figure 1:
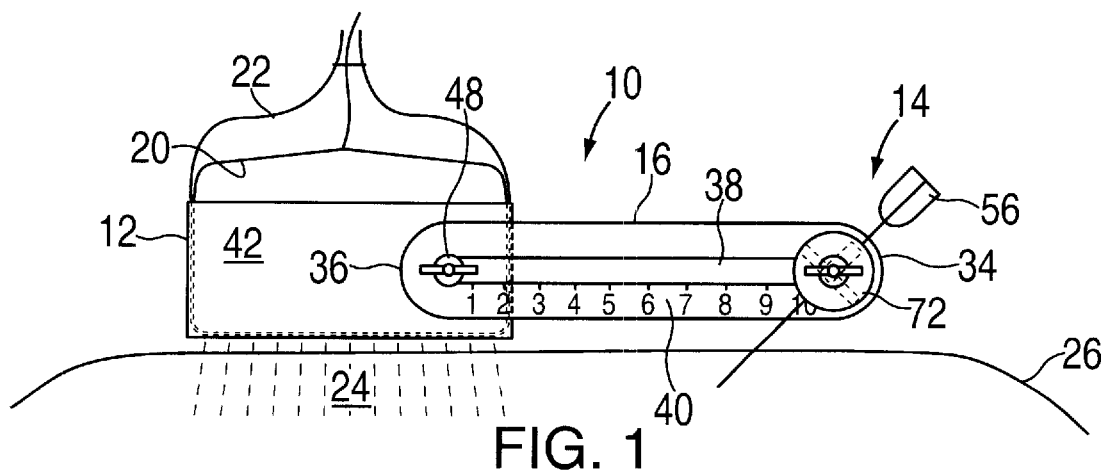
FIG. 1 is a side view of the present invention.
Figure 2:
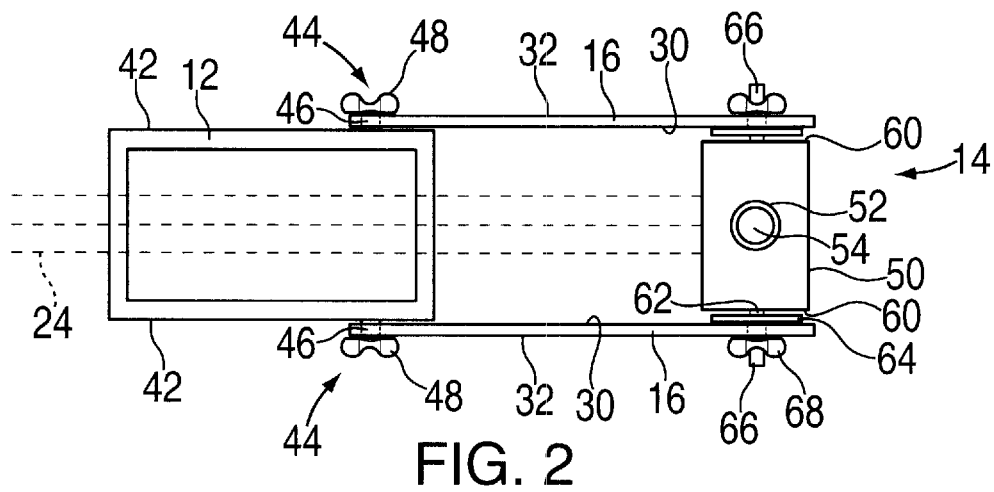
FIG. 2 is a top view of the invention in FIG. 1.
Figure 3:
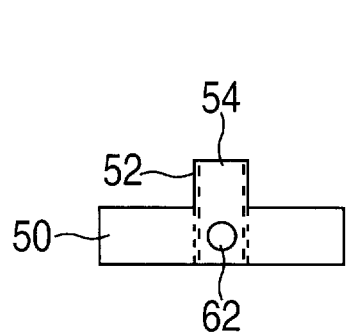
FIG. 3 is a side view of a preferred needle guide unit.
Figure 4:
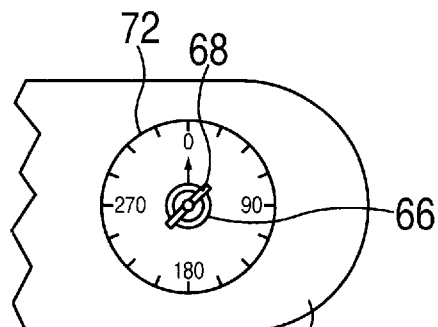
FIG. 4 is a side view of the protractor of the needle guide unit.

As shown in FIGS. 1 and 2, needle guidance apparatus 10 comprises box-shaped frame 12, needle guide unit 14, and two, parallel arms 16. Transducer 20 in latex bag 22 is securely held in frame 12 because of the frictional fit between the inside walls of frame 12 and the outside surface of transducer 20. Transducer 20 generates ultrasound beam 24 which is a planar beam that is vertically oriented in FIG. 1. Transducer 20 in frame 12 is held against body 26 of a patient.

Each arm 16 is generally rectangular in shape having vertical, flat inside wall 30, vertical, flat outside wall 32, two ends 34 and 36, and slot 38 therein which runs lengthwise in arms 16. Associated with each slot 38 is a gauge 40 for measuring and adjusting the distance or location between frame 12 and needle guide unit 14.

Frame 12 has vertical, flat outside walls 42. Extending outward from walls 42 is releasable fastener 44 which comprises bolt 46 with a respective wing nut 48. Bolt 46 extends from walls 42 of frame 12 through slot 38. Wing nut 48 is tightened to secure the position of frame 12 in slot 38. Because walls 30 and 42 are vertical and flat against each other when wing nut 48 is tightened, a secure stable arrangement is made between arms 16 and frame 12.

Needle guide unit 14 has a generally rectangular shaped base 50 with a sleeve 52 therein. Sleeve 52 has bore 54 through which needle 56 is inserted. Sleeve 52 is coplanar with ultrasound beam 24. Extending outward from opposite sides 60 of base 50 is inner shaft 62 and washer 64. Base 50 rotates about inner shaft 62 while washer 64 remains in place. Extending outward from washer 64 is outer shaft 66 upon which wing nut 68 is attached. Outer shaft 66 is affixed to washer 64 while inner shaft 62 rotates freely, thereby allowing base 50 to rotate. Tightening wing nut 68 on outer shaft 66 fixes the position of needle guide unit 14 in slot 38, but allows needle guide unit 14 to pivot because inner shaft 64 rotates against washer 64. Outer shaft 66 and wing nut 68 make up a releasable fastener.

Washer 64 when held tightly against inside wall 30 causes a secure and stable arrangement between needle guide unit 14 and arms 16 because both form flat, vertical surfaces against each other.

Positioned on outer shaft 66 is protractor 72 to measure the angle of insertion of needle 56. As can be seen, 0° on protractor 72 is aligned with sleeve 52 and bore 54 when they are vertical.

The horizontal distance between frame 12 and needle guide unit 14 can vary because both travel in slot 38 and are releasable fastened to arms 16. The overall orientation of frame 12 with transducer 20 therein and needle guide unit 14 with needle 56 therein is maintained because of the interaction between flat inside wall 30 of arms 16 and flat outside wall 42 of frame 12 and because of washer 64 of needle guide unit 14 and flat inside wall 30 of arms 16. Washer 64 forms an outer wall of needle guide unit 14. Because outside walls 42 of frame 12 and inside wall of washer 64 of needle guide unit 14 are vertical and parallel to vertical inside wall 30 of arms 16, a secure, strong apparatus is formed.

Protractor 72 can rotate with base 50 by being attached to inner shaft 62 or protractor 72 can be affixed to outer shaft 66 and, thus, not rotate with base 50. When protractor 72 is affixed to outer shaft 66, a user must align needle 56 with the scale on protractor 72 to determine the angle of insertion.

FIGS. 5–14 show different embodiments for arms 16.

Figure 5:
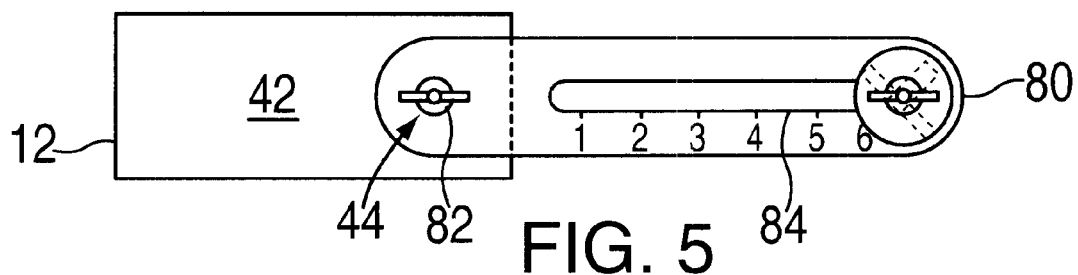
FIG. 5 is a side view of another arm design.

In FIG. 5, arms 80 have a single hole 82 through which bolt 46 passes. Arms 80 are affixed to frame 12 by releasable fastener 44. Slot 84 allows needle guide unit 14 to slide. so as to vary the horizontal distance between frame 12 and needle guide unit 14.

Figure 6:
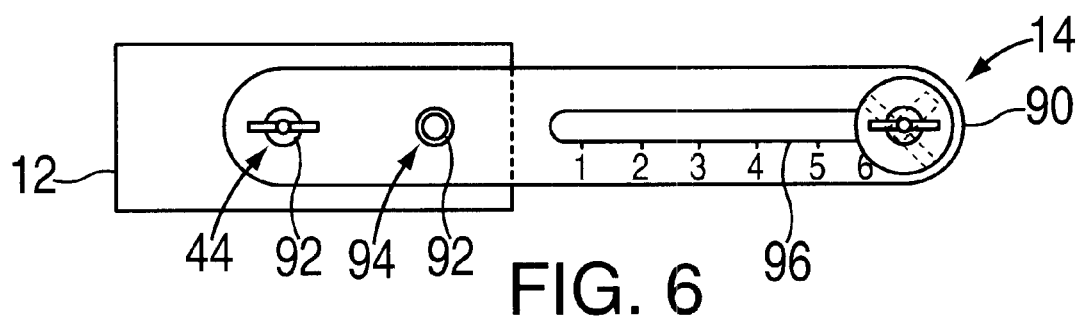
FIG. 6 is a side view of yet another arm design.

In FIG. 6, arms 90 have two holes 92. Through one hole 92 bolt 46 extends and allows releasable fastener 44 to fix frame 12 to arms 90. Through the other hole 92 a dowel 94 extends. Slot 96 has needle guide unit 14 releasably affixed therein.

Figure 7:
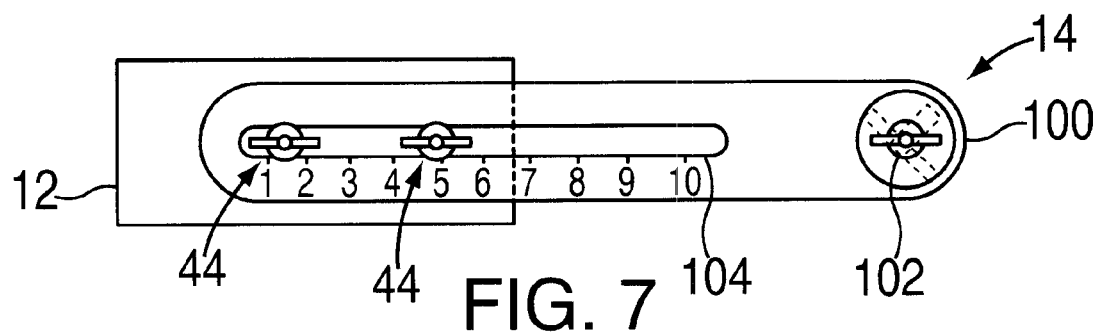
FIG. 7 is a side view of a further arm design.

In FIG. 7, arms 100 have one hole 102 through which needle guide unit 14 is rotatably mounted by means of inner shaft 62. Frame 12 is releasably affixed by means of releasable fastener 44 in slot 104 to arms 100. One of the fasteners in FIG. 7 can be a dowel similar to dowel 94 of FIG. 6. Using two fasteners or a dowel and a fastener in slot 104 helps maintain the horizontal position of the arms.

Figure 8:
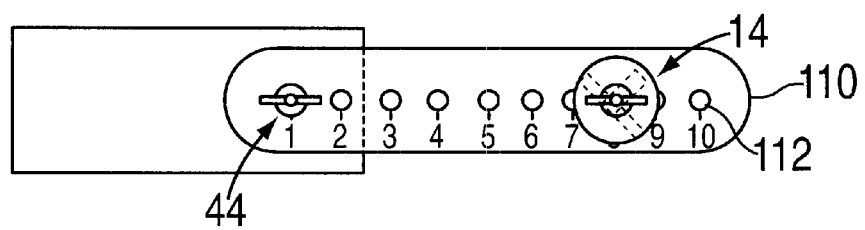
FIG. 8 is a side view of still a further arm design.

In FIG. 8, arms 110 employ a plurality of holes 112 instead of a slot. Each of holes 112 are numbered to act in a similar manner to gauge 40. Frame 12 and needle guide unit 14 can move horizontally with respect to one another by moving the hole in which they are fastened to arms 110. Frame 12 can be releasably affixed to arm 110 by means of either one dowel and one fastener or two fasteners.

Figure 9:
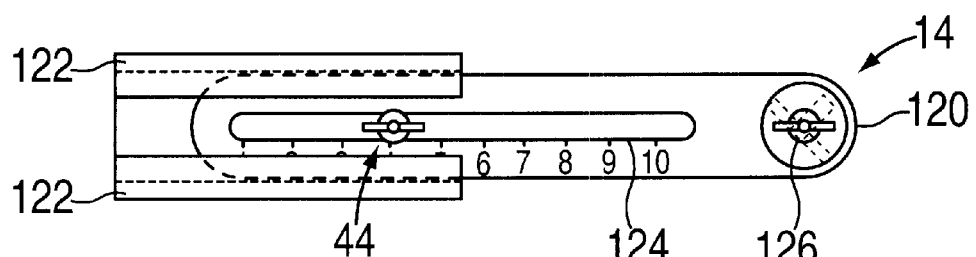
FIG. 9 is a side view of a fastener arrangement between the frame and the arm.
Figure 10:
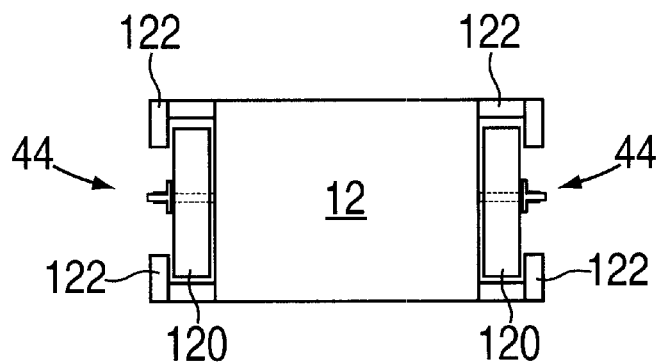
FIG. 10 is another side view of the frame of FIG. 9.

In FIGS. 9 and 10, arms 120 slide between rails 122 thereby maintaining arms 120 in a horizontal position. Slot 124 allows frame 12 to be releasably affixed to arms 120 and hole 126 allows needle guide unit 14 to pivot with respect to arm 120. Rails 122 are affixed to side walls 42 of frame 12.

Figure 11:
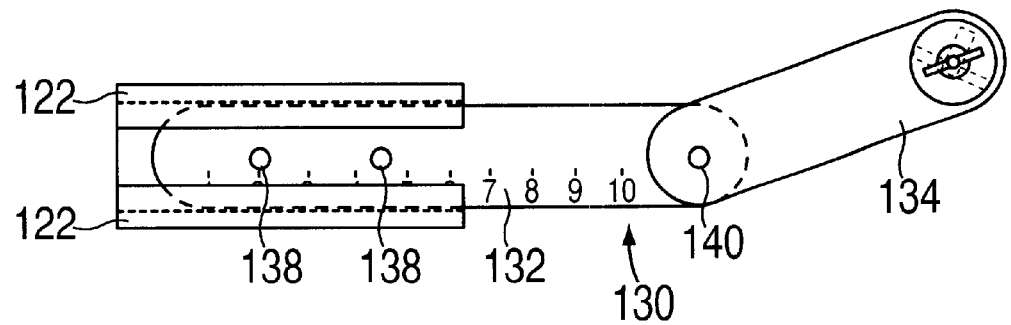
FIG. 11 is a side view of a different arm design.
Figure 12:
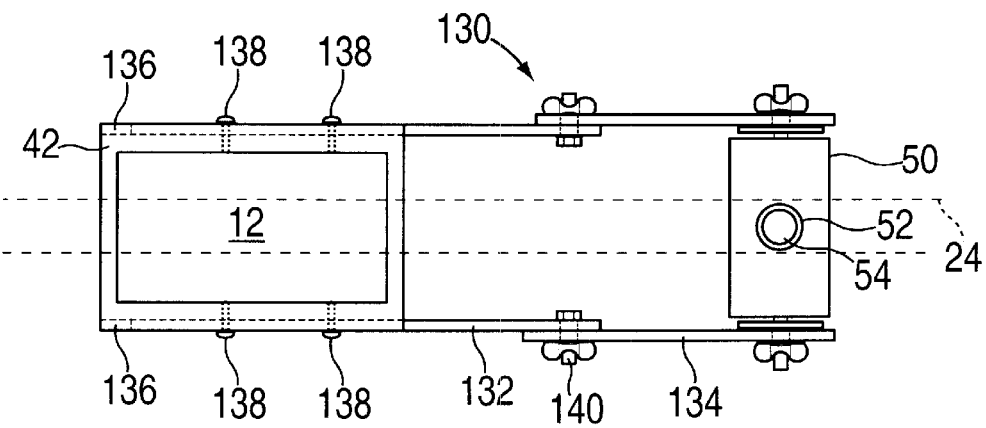
FIG. 12 is a top view of FIG. 11

In FIGS. 11 and 12, arms 130 are each comprised of horizontally fixed arms 132 and pivotal arms 134. Fixed arms 132 slide in rails 122 which are affixed to side walls 42 of frame 12. Set screws 138 fix the position of horizontal arms 132. Pivotal arms 134 pivot on joints 140 which are suitably a nut and bolt arrangement through respective holes in arms 132 and 134. Needle guide unit 14 is affixed at one end of pivotal arms 134.

Figure 13:
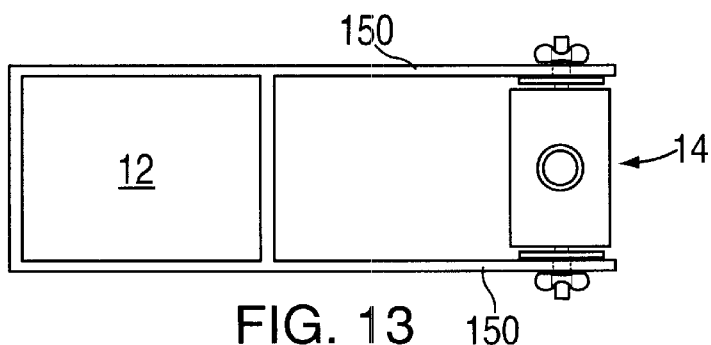
FIG. 13 is a top view of the apparatus where the arms are integral with the frame.
Figure 14:
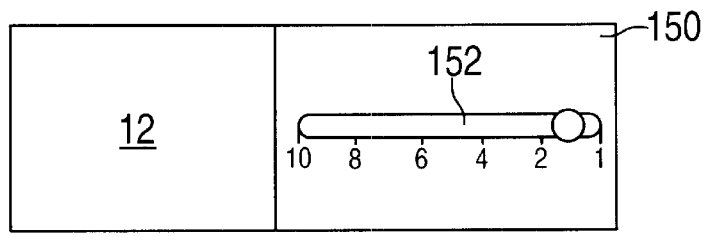
FIG. 14 is a side view of the apparatus of FIG. 14.

In FIGS. 13 and 14, arm 150 is part of frame 12, while guide unit 14 moves in slot 152.

Figure 15:
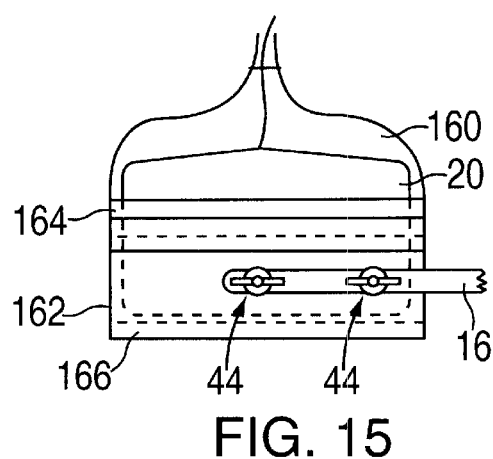
FIG. 15 is a side view of a latex sleeve and frame enclosing the transducer.

In FIG. 15, latex sleeve 160 is held onto frame 162 by tape 164. In this configuration, frame 162 has bottom 166, thus, when sleeve 160 is tied around the cord of transducer 20, sleeve 160 in conjunction with frame 162 encloses transducer 20.

Frame 12 is FIGS. 1–2 and 5–14 can have a closed bottom or be open. When the base of frame 12 is open, latex bag 22 encloses transducer 20.

Preferably, the apparatus of the present invention is made from plastic which is intended for a single use and then thrown away or recycled. Alternatively, the apparatus of the present invention is sterilized and reused, however, one of skill in the art will realize that the apparatus of the present invention need not be sterilized before reuse. In such an embodiment, the preferred arrangement is the one that is least expensive to manufacture.

Different arrangements of affixing the frame and the needle guide unit to the arm have been shown in the drawings. It will be appreciated that either a slot, holes, or a combination of both can be employed for either or both the frame and the needle guide unit. Furthermore, the frame can be attached to the arm by means of a pair of rails with or without set screws as shown in FIG. 11.

The apparatus of the present invention is suitably made from material that can be easily sterilized such as stainless steel or plastic as noted above.

It will be understood that the claims are intended to cover all changes and modifications of the preferred embodiments of the invention herein chosen for the purpose of illustration which do not constitute a departure from the spirit and scope of the invention.

What is claimed is:

1. A needle guidance apparatus for use with an ultrasound imaging device that generates a substantially planar ultrasound beam from one end of a transducer comprising:
   (a) a box-shaped frame for securely holding a transducer when the frame with the transducer therein is placed against the body of a patient;
   (b) a needle guide unit having a sleeve for accommodating and guiding a needle into the body of a patient, said sleeve being coplanar with an ultrasound beam from said transducer, and said needle guide unit pivotal about a transverse axis; and
   (c) two parallel arms, one end of each of said arms attached to opposite sides of said frame and the other end of each of said arms attached to opposite sides of said needle guide unit, said frame or said needle guide unit or both said needle guide unit and said frame being movable with respect to said arms such that the horizontal distance between said needle guide unit and said frame can vary.

2. The apparatus of claim 1 wherein each of said arms has a slot that runs from one end to the other end in a horizontal direction, a first releasable fastener is positioned in each slot and attached to said frame for releasably affixing said frame to said arms, and a second releasable fastener is attached to said needle guide unit and positioned in said slot for releasably affixing said needle guide unit to said arms.

3. The apparatus of claim 2 wherein two first releasable fasteners are attached to said frame and positioned in each slot for releasably affixing said frame to said arms.

4. The apparatus of claim 2 wherein a dowel is affixed to said frame and positioned in each of said slots along with said first releasable fastener.

5. The apparatus of claim 1 wherein each of said arms has a plurality of holes that run from one end to the other end in a horizontal direction, a first releasable fastener is affixed to said frame and positioned in one of said holes in said arms for releasably affixing said frame to said arms, and a second releasable fastener is positioned in each slot and attached to said needle guide unit for releasably affixing said needle guide unit to said arms.

6. The apparatus of claim 1 wherein said transducer is in a latex bag.

7. The apparatus of claim 1 wherein said frame has a closed bottom and a latex sleeve is affixed to said frame such that said transducer is enclosed by said frame and said sleeve.

8. The apparatus of claim 1 wherein said arms are affixed to said frame and said needle guide unit is movable.

9. The apparatus of claim 8 wherein said arms are part of said frame.

10. The apparatus of claim 8 wherein said arms have a slot and said needle guide unit moves in said slot.

11. The apparatus of claim 1 wherein said frame has a pair of guide rails on opposite sides of said frame in which said arms travel.

12. The apparatus of claim 11 wherein said arms are held against said frame by set screws and said rails.

13. The apparatus of claim 1 wherein each of said arms comprise a horizontal fixed arm and a movable arm, said fixed arm adjacent said frame and said movable arm adjacent said needle guide unit and said fixed arm attached to said movable arm by a releasable fastener.

* * * * *